(12) United States Patent
Winkler, Sr. et al.

(10) Patent No.: US 9,724,260 B2
(45) Date of Patent: Aug. 8, 2017

(54) COMPRESSION GARMENT

(71) Applicant: Compression Dynamics LLC, Omaha, NE (US)

(72) Inventors: Martin J. Winkler, Sr., Omaha, NE (US); Alan S. Neil, Indian Shores, FL (US)

(73) Assignee: Compression Dynamics, LLC, Omaha, NE (US)

( * ) Notice: Subject to any disclaimer, the term of this patent is extended or adjusted under 35 U.S.C. 154(b) by 515 days.

(21) Appl. No.: 14/212,186

(22) Filed: Mar. 14, 2014

(65) Prior Publication Data

US 2014/0200494 A1 Jul. 17, 2014

Related U.S. Application Data

(63) Continuation-in-part of application No. 11/063,114, filed on Feb. 22, 2005, now abandoned, and a continuation of application No. 12/291,654, filed on Nov. 12, 2008, now Pat. No. 8,034,013, and a continuation-in-part of application No. 13/223,111, filed on Aug. 31, 2011, now Pat. No. 8,641,653, and a continuation-in-part of application No. 14/170,846, filed on Feb. 3, 2014, now Pat. No. 9,259,373.

(60) Provisional application No. 61/794,157, filed on Mar. 15, 2013.

(51) Int. Cl.
*A61L 15/00* (2006.01)
*A61H 1/00* (2006.01)
*A61F 13/08* (2006.01)

(52) U.S. Cl.
CPC ............. *A61H 1/008* (2013.01); *A61F 13/08* (2013.01)

(58) Field of Classification Search
CPC . D04B 9/54; D04B 1/18; D04B 1/106; D04B 1/26; D04B 21/18; D04B 1/24; D04B 21/12; D04B 9/10; D04B 21/207; D04B 35/04; D04B 1/243; D04B 21/06; D04B 21/16; D04B 7/06; D04B 9/20; A61F 13/08; A61F 13/0273; A61F 13/069; A61F 13/00991; A61F 13/0283; A61F 13/00017; A61F 13/00038; A61F 13/00046; A61F 13/06; A61F 13/085; A61F 13/108; A61F 2013/00119; A61F 2013/00; A61H 1/008
USPC ................................................ 602/60, 75, 62
See application file for complete search history.

(56) References Cited

U.S. PATENT DOCUMENTS

| | | |
|---|---|---|
| 3,306,288 A | 2/1967 | Rosenfield |
| 3,409,008 A | 11/1968 | Mortensen et al. |
| 3,570,482 A | 3/1971 | Emoto et al. |
| 3,728,875 A | 4/1973 | Hartigan et al. |
| 3,747,374 A | 7/1973 | Meyer |
| 4,015,448 A | 4/1977 | Knohl |
| 4,377,160 A | 3/1983 | Romaine |
| 4,424,808 A | 1/1984 | Schafer et al. |

(Continued)

*Primary Examiner* — Michael Brown
(74) *Attorney, Agent, or Firm* — Mallory M. Henninger; Advent, LLP

(57) ABSTRACT

A graduated compression garment is disclosed that includes a plurality of longitudinal fuzzy wales arranged to form a fabric with a plurality of transverse elastomeric threads under variable tension connecting the adjacent longitudinal fuzzy wales to deliver a first level of elastic compression distally on a limb and a gradually decreasing level of elastic compression as the limb increases in diameter proximally.

10 Claims, 9 Drawing Sheets

(56) References Cited

U.S. PATENT DOCUMENTS

| | | | |
|---|---|---|---|
| 4,520,635 A * | 6/1985 | Shields | A41B 11/02 |
| | | | 2/239 |
| 4,657,003 A | 4/1987 | Wirtz | |
| 4,832,010 A | 5/1989 | Lerman | |
| 5,257,956 A | 11/1993 | Ewen | |
| 5,344,406 A | 9/1994 | Spooner | |
| 5,695,452 A | 12/1997 | Grim et al. | |
| 5,735,807 A | 4/1998 | Cropper | |
| 6,311,334 B1 | 11/2001 | Reinhardt et al. | |
| 6,435,221 B1 | 8/2002 | Waldrop et al. | |
| 7,867,185 B2 * | 1/2011 | Lipshaw | A61F 13/08 |
| | | | 602/60 |
| 8,034,013 B2 | 10/2011 | Winkler | |
| 8,641,653 B2 | 2/2014 | Winkler | |
| 2006/0189913 A1 | 8/2006 | Winkler | |
| 2007/0179421 A1 * | 8/2007 | Farrow | A61H 9/005 |
| | | | 602/75 |
| 2014/0148742 A1 | 5/2014 | Winkler | |
| 2015/0150710 A1 * | 6/2015 | Evans | A61F 13/00017 |
| | | | 602/6 |

* cited by examiner

COMPRESSION GARMENT

CROSS-REFERENCE TO RELATED APPLICATIONS

The present application is a continuation-in-part of and also claims the benefit of U.S. Non-Provisional application Ser. No. 11/063,114 filed Feb. 22, 2005. Said U.S. Non-Provisional application Ser. No. 11/063,114 filed Feb. 22, 2005 is hereby incorporated by reference in its entirety.

The present application is a continuation of and also claims the benefit of U.S. Non-Provisional application Ser. No. 12/291,654 filed Nov. 12, 2008 (now U.S. Pat. No. 8,034,013). Said U.S. Non-Provisional application Ser. No. 12/291,654 filed Nov. 12, 2008 is hereby incorporated by reference in its entirety.

The present application is a continuation-in-part of and also claims the benefit of U.S. Non-Provisional application Ser. No. 13/223,111 filed Aug. 31, 2011 (now U.S. Pat. No. 8,641,653). Said U.S. Non-Provisional application Ser. No. 13/223,111 filed Aug. 31, 2011 is hereby incorporated by reference in its entirety.

The present application is a continuation-in-part of and also claims the benefit of U.S. Non-Provisional application Ser. No. 14/170,846 filed Feb. 3, 2014. Said U.S. Non-Provisional application Ser. No. 14/170,846 filed Feb. 3, 2014 is hereby incorporated by reference in its entirety.

The present application claims the benefit of U.S. Provisional Application Ser. No. 61/794,157 filed Mar. 15, 2013. Said U.S. Provisional Application Ser. No. 61/794,157 filed Mar. 15, 2013 is hereby incorporated by reference in its entirety.

TECHNICAL FIELD

The present disclosure relates to medical garments. More specifically, the disclosure relates to therapeutic compression garments.

BACKGROUND

Therapeutic garments and stockings are well known in the art and come in various configurations and are put to various uses. Compression therapy is primarily used for treating leg ulcers, treating dermatitis due to venous insufficiency (failure of veins and their valves to return blood to the heart), and treating congenital and acquired lymph edema and for treating edema due to congestive heart failure.

Compression Garment

It is an aspect of one embodiment of the disclosure to provide a tubular graduated compression garment. More specifically, the disclosure relates to tubular graduated therapeutic compression garments for the graduated control of excess water in the subcutaneous fat. Manifestations of the present disclosure include providing graduated therapeutic elastic compression garments with fuzzy wales 14 designed to move water out of fat below the skin.

It is a further aspect of an additional embodiment of the disclosure to provide a measuring device for measuring and fitting a graduated tubular compression garment.

Other features and advantages of the disclosure will be apparent from the following specification taken in conjunction with the following drawings.

BRIEF DESCRIPTION OF THE DRAWINGS

To understand the present disclosure, it will now be described by way of example, with reference to the accompanying drawings in which.

DETAILED DESCRIPTION

Figure 1:
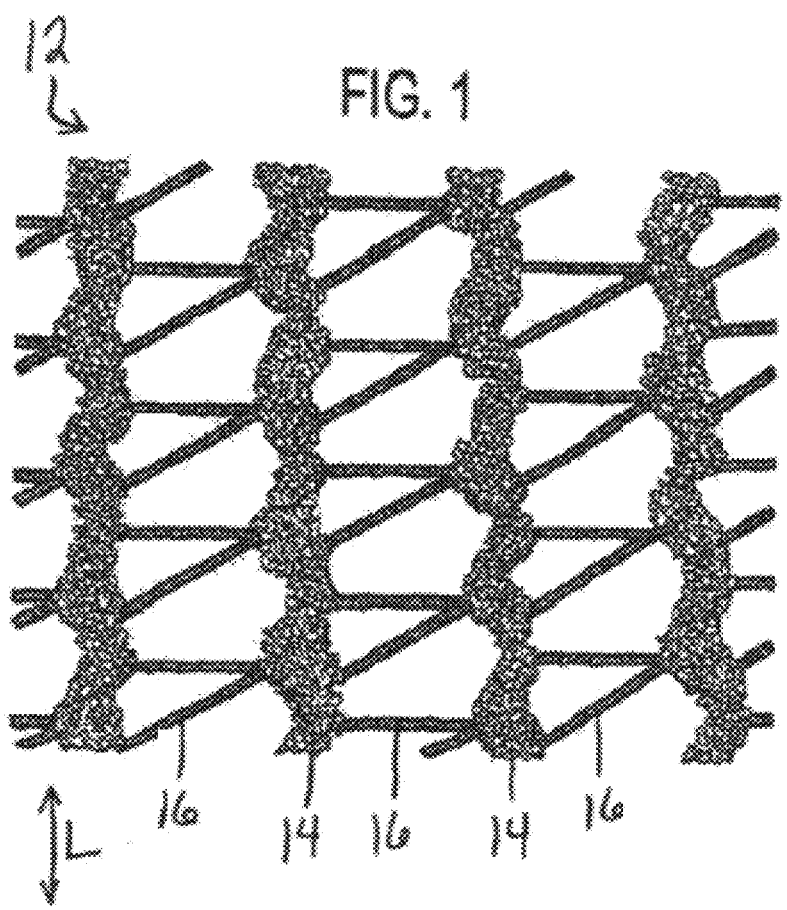
FIG. 1 is a plan view of a fabric constructed according to the present disclosure in a stretched state.

While this disclosure is susceptible of embodiments in many different forms, there is shown in the drawings and will herein be described in detail preferred embodiments of the disclosure with the understanding that the present disclosure is to be considered as an exemplification of the principles of the disclosure and is not intended to limit the broad aspect of the disclosure to the embodiments illustrated.

It is an aspect of one embodiment of the disclosure to provide a graduated compression garment 40 comprising a plurality of longitudinal wales 14 arranged to form a fabric having a length and generally parallel to the length. The garment has a plurality of lateral elastomeric threads 16 connecting adjacent longitudinal wales 14 and equally spaced about a length of the longitudinal wales 14 where, in a stretched state, the longitudinal wales 14 are spaced from one another and remain generally parallel to the length. The longitudinal wales 14 may have a fuzzy outer surface and/or a larger diameter than the lateral threads 16.

It is a further aspect of one embodiment of the disclosure to provide that when the garment is worn by a patient and in contact with and applying compression to a skin of the patient and in a stretched state such that each longitudinal wale is spaced from any adjacent longitudinal wale, each longitudinal wale presses into the skin and the skin stents each longitudinal wale by forming a longitudinal furrow in the skin that receives the longitudinal wale, the furrow tending to prevent relative movement of each longitudinal wale with respect to the skin.

In an additional embodiment of the disclosure, a device includes, but is not limited to, a plurality of substantially parallel primary wales 14 in a substantially longitudinal formation; a plurality of secondary transverse elastomeric threads 16 between at least two of the plurality of substantially parallel primary wales 14 and substantially equally spaced about a length of the plurality of primary wales 14, the adjacent primary wales 14 and secondary transverse elastomeric threads 16 connected to form a generally tubular configuration, the plurality of secondary transverse elastomeric threads 16 connected to adjacent primary wales 14 at an angle greater to or less than 90 degrees with respect to the plurality of substantially parallel primary wales 14, and maintaining a continuous longitudinal arrangement of the plurality of substantially parallel primary wales 14 during any stretch state of the plurality of substantially parallel primary wales 14.

Figure 2:
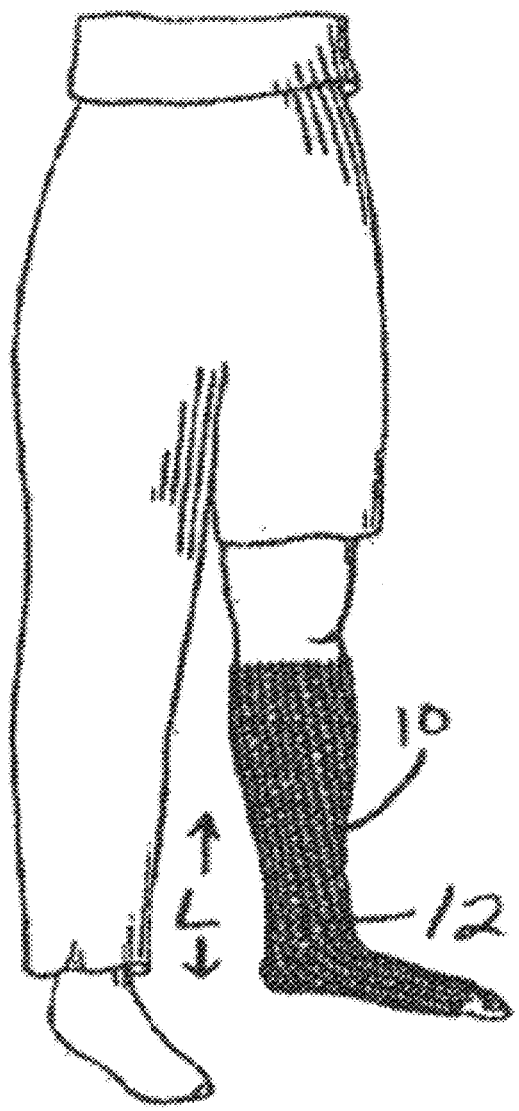
FIG. 2 shows a therapeutic compression dressing or garment 10 according to the present disclosure having a generally tubular form.

FIG. 2 shows a therapeutic compression dressing or garment 10 according to the present disclosure having a generally tubular form. The fabric 12 from which the tubular compression garment 10 is formed is shown in more detail in FIG. 1. It can be seen that the fabric 12 includes a plurality of primary or longitudinal wales 14 and a plurality of secondary, lateral or connective wales 14 16. The primary wales 14 are arranged to be substantially parallel with a longitude L of the tubular compression garment 10. The secondary transverse elastomeric threads 16 extend between and connect adjacent primary wales 14, to be further described. The secondary transverse elastomeric threads 16 are arranged to be secondary to the longitude L. It can be seen that in the embodiment shown in the figures, the secondary transverse elastomeric threads 16 are arranged at an angle other than about 90 degrees to the longitude L.

The fabric 12 is knitted using a criss-crossing lateral stitch on a warp knitting machine. For instance, at least a portion of the plurality of substantially parallel primary wales 14 and the plurality of secondary transverse elastomeric threads 16 may be formed from a criss-crossing lateral stitch on a warp knitting machine to form the plurality of substantially parallel primary wales 14 and the plurality of secondary transverse elastomeric threads 16. A resulting typical tube of fabric 12 includes 60 continuous longitudinal wales 14 connected by a plurality of secondary or lateral wales 14 16. Because of the six course repeat chain stitch that is used, when a tube of fabric 12 is stretched radially about any length of the fabric 12, the longitudinal wales 14 maintain their longitudinal orientation with respect to the overall tube of fabric 12. This is in contrast to other fabrics that may arguably include longitudinal wales 14 and lateral elastomeric threads 16 in an initial or relaxed state, wherein when stretched, the longitudinal wales 14 become arranged at an angle to the longitude of a tube made from the fabric.

In one preferred embodiment, and as shown, the primary or longitudinal wales 14 comprise a standard 3 ply 70 nylon wale having mild longitudinal recovery. One or more individual longitudinal wales 14 of the plurality of longitudinal wales 14 may be formed from medical grade nylon knitted wales 14 arranged to form a fabric cylinder having a length and generally parallel to the length. The longitudinal wale material may comprise a plurality of light or fine fibers surrounding a core fiber. The plurality of light or fine fibers may produce a substantially fuzzy effect. The longitudinal wale 14 is capable of being stretched between a first unstretched length and a second or stretched position with a fully stretched length being approximately 350% longer than the unstretched length. Specifically, in a stretched state, (e.g., when deployed on a human extremity or torso of proper size), the longitudinal wales 14 may be spaced with a ratio of about four wale diameters between one another and remain generally parallel to the length.

The secondary transverse elastomeric threads 16 generate elastic compression in a starched state and are typically made from a polymer containing polyurethane such as commercially available spandex products. It is important to note that the diameter of each longitudinal wale 14 is significantly larger than the diameter of each secondary thread 16. Preferably, the diameter of the longitudinal wale 14 is approximately 11 times larger than the diameter of the secondary elastomeric spandex thread. The plurality of elastomeric threads 16 may be elastomeric (e.g., spandex) or like elastic material and may connect adjacent longitudinal to form a fabric cylinder of longitudinal fuzzy wales 14 equally spaced about a length of the longitudinal wale.

When a patient dons the compression garment 10, the fabric 12 stretches creating space between adjacent longitudinal wales 14. Because of the elastic nature of the lateral threads 16, each longitudinal wale 14 exerts a compression force on the skin or surface of the patient's limb, only at the point of contact between the longitudinal wale 14 and the skin. Actually, the "point of contact" is in fact a line of contact between the wale 14 and the skin, about the length of the longitudinal wale 14. Because of the disparity in the size of diameter of the primary wale 14 and the secondary elastomeric threads 16, the secondary, or lateral wales 14 16, do not exert any pressure directly on the limb in comparison to the pressure exerted by the longitudinal wales 14.

This has at least two effects. First the construction of the fabric 12 virtually eliminates any tourniquet effects obstructing the arterial, venous and lymphatic vessels in the subcutaneous fat found in prior art garments. Second, because in cross section, the longitudinal or linear compression exerted by the longitudinal wale 14 is felt by the limb at only discreet points about its circumference, it has been found that patients are much better able to tolerate higher compression forces. This, in turn, allows compression garments 10 constructed of fabric 12 according to the present disclosure to utilize greater pressures sufficient to assist the deeper popliteal vein 22 in also removing fluid from the affected area.

Figure 3:
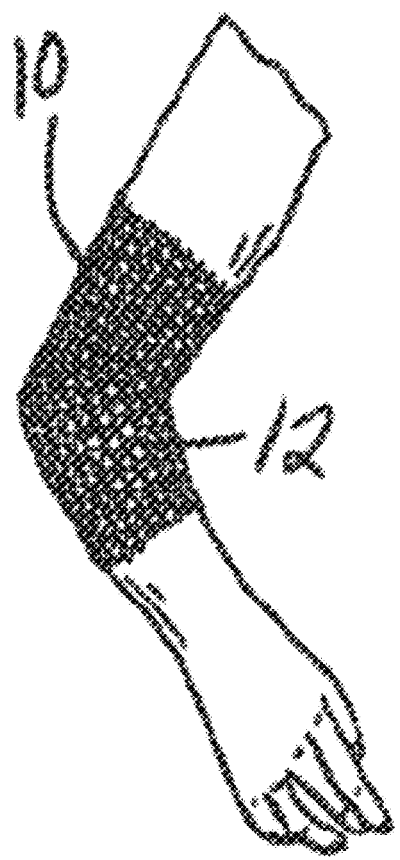
FIG. 3 shows an additional embodiment of a therapeutic compression garment according to the present disclosure having a generally tubular form.

As noted, the fabric 12 of the present disclosure may be used to create a tubular stocking to assist in treating the feet, ankles or any portion of the legs. The fabric 12 may also be used to form a sleeve (e.g., FIG. 3) for treating the knee or elbow area; or the fabric 12 may be used to form a closed end tube for treating and assisting in swelling reduction for stumps in amputation situations. Additionally, it has been found that the fabric 12 of the present disclosure is effective in treating and reducing the appearance of cellulite and therefore the fabric 12 may be used to form a pair of shorts extending down all or a portion of the thighs or a pair of tights extending down the entirety of the legs.

The following is a discussion of the functionality of the present disclosure. The primary or longitudinal wale 14 alone is essentially in contact with the skin. Of course, the lateral elastomeric threads 16 also occasionally come into contact with the skin, but the lateral threads 16 do not exert any effective pressure on the extremity. The primary wales 14 have a soft or fuzzy outer surface. This fuzzy surface molds to the micro geography of the skin surface and "stents" the skin. Skin stenting will be further discussed below. The longitudinal fuzzy wale 14 stents the skin holding the wale 14 in place over a small strip of skin cells. The longitudinal wales 14 do not move relative to furrows 32 of skin formed beneath the longitudinal wales 14, even with motion of the extremity. This prevents shearing injuries to the skin.

The longitudinal fuzzy wale 14 may also provide both skin insulation and cooling. For instance, the plurality of substantially parallel primary wales 14 may be formed from a material capable of raising the temperature of a region of skin in contact with the plurality of substantially parallel primary wales 14. In some instances, the longitudinal wale 14 insulates the skin and generally raises the skin temperature one to three degrees F. It is known that elevating the skin temperature slightly can significantly increase blood flow to the feet of patients with arterial occlusive disease. Therefore, a compression garment 10 according to the present disclosure tends to improve skin perfusion by warming the skin. However, the compression garment may be cooling in warm environments as 75% of the skin is open to allow heat to radiate, as well as breathable to allow sweat to evaporate from exposed skin.

The longitudinal wales 14 in the fabric 12 of the present disclosure tends to create skin furrows or "cornrows," as noted above. The furrows may reach a maximum depth of 1.5 to 2.0 times the radius of the longitudinal wale 14. The longitudinal wale 14 "presses in" and forms the furrows in the skin. These furrows provide significant benefit to the patient. The secondary or lateral elastomeric threads 16 transmit tension/compressive forces to the longitudinal wales 14. The longitudinal wales 14 are thereby "stented" in place by the skin over a given small surface of skin. The longitudinal wales 14 focus compressive force on a small area of skin. Elastic compression presses the longitudinal wale 14 into the skin and the furrows form in the skin. The convex cross section of the longitudinal wale 14 acts to focus compressive force somewhat like the point of a nail, focusing the energy of a hammer blow onto a tiny surface, creating infinite pressure that drives the nail to pass through, for example, solid oak. Similarly, the skin in the furrow beneath the convex cross section of the longitudinal wale 14 experiences physiologically significant pressure.

The fuzzy outer surface of the wale may substantially stent and protect the skin in immediate contact with the fuzzy surface, creating a fuzzy skin nexus, while applying compression to the skin in contact with the fuzzy wale. Thus, when worn, a surface of a wearer's skin is in contact with a fuzzy skin nexus, and the fuzzy wale skin nexus applies a force of compression to the skin.

The secondary elastomeric fibers provide only the force of tension between wales 14. The secondary elastomeric fibers for the most part are not in functional contact with the skin. When in a state of tension, the secondary elastomeric fibers provide a skin surface geography with a ratio of compressed skin surface to substantially uncompressed skin surface of about one to five between adjacent longitudinal wales 14.

Under the force of elastomeric fiber tension, each longitudinal wale forms a longitudinal furrow in the skin that acts a biological stent. Specifically, under the force of the lateral elastomeric fiber tension, each longitudinal wale presses into the skin and the stents the skin. This compression of the skin forms a "corn row" furrow in the skin beneath the fuzzy nexus of each longitudinal wale. Also, under the force of elastomeric fiber tension, the longitudinal wale forming a longitudinal furrow in the skin tends to prevent relative movement of each longitudinal wale with respect to the skin.

Fixed fuzzy longitudinal wales 14 stretch the connected secondary spandex elastomeric threads 16. The elastomeric spandex fibers are substantially under only the force of tension and interact with the fuzzy longitudinal wales 14 which are substantially under only the force of compression. Secondary elastomeric (e.g., spandex) threads 16 under tension between fixed fuzzy wales 14 under compression create a tensegrity structure. This tensegrity structure, comprising a plurality of longitudinal wales 14, fixed in skin cornrow furrows, under the force of compression, and secondary elastomeric spandex threads 16, under only the force of tension, translates limb motion into changes in the length of the elastomeric components. Changes in elastic thread length changes the compression delivered to the skin via longitudinal wales 14 resting in skin furrows. Limb motion changes in the pressure of compression evidenced by the stented skin in cornrow furrows. Pressure changes in the sub cutaneous fat beneath the skin caused by motion of the wearer drives lymphatic pumping of lymph fluid.

The compression garment comprises a generally tubular stocking that has a "fuzzy nexus" with at least one fifth of the surface of the covered portion of a wearer's skin. That is, the 20 percent portion of the skin surface is under physiologically useful compression. Indentations, furrows, form in the 20 percent portion of the skin surface as a result of the force of compression. The compression garment also provides four fifths of the skin, between fuzzy wales 14, that is uncompressed. This uncompressed skin acts as a Sink for venous and lymphatic effluent drainage from the compressed skin, provides uncovered skin surface for evaporation of sweat, and provides uncovered skin surface for radiation of heat.

On a microscopic level, the following events occur in the skin beneath the longitudinal wale 14 in the furrow 32:

1.) The thin walled lymphatic vessels in the fat beneath the skin are compressed and the lymph fluid in these vessels is pushed/squeezed/wrung out by the external pressure delivered by the longitudinal fuzzy longitudinal wale 14. Skin lymphatic vessels and skin veins have one way valves. Skin pressure changes in this valved tissue vascular structure produce a venous and a lymphatic "physiologic pump" that clears swelling from the skin and subcutaneous fat. Lymph fluid in healthy legs is pumped back to the heart from the feet with increased pressure gradients of 1 to 3 centimeters of water. Garments or dressings 10 created with the fabric 12 according to the present disclosure deliver a pressure to the sub dermal fat in excess of 3 centimeters of water in a "halo" 74 of pressure that extends out from the skin furrow 32 beneath each longitudinal wale 14 and deeper into the fat below the skin than is possible with prior art compression devices. This halo 74 of pressure, from a cellular point of view, penetrates the fat much deeper than pressure from older compression garments is able to penetrate. This halo 74 of pressure, exceeding three centimeters water, extends far into the tissue around the furrow 32. In this deeply penetrating halo 74 of high pressure, lymphatic flow is greatly enhanced.

2.) The thin walled veins in the fat beneath the longitudinal wales 14 are emptied of their fluid which constitutes deoxygenated blood rich in lactic acid. Veins in the lower extremity may require pressure gradients of 5 to 15 centimeters of water to return fluid toward the heart. Garments or dressings 10 created with the fabric 12 according to the present disclosure may deliver pressure in excess of 15 centimeters of water in a halo 74 of high pressure around the longitudinal wale 14/skin furrow 32. The cells beneath the longitudinal wale 14 in the zone of pressure above 15 cm of water experience the following: perfusion by arterial blood in the capillaries; pressurized arterial blood is the only fluid that can enter the 74 of >15 centimeter/water tissue pressure. This halo 74 of >15 centimeter pressure causes rapid out flow of venous blood and lymphatic fluid, and causes elevated oxygen tension in the tissues. The halo 74 of >15 centimeter pressure penetrates the fat much deeper than can pressure generated by older compression devices because the compressive energy is focused by the fluffy longitudinal wale 14 stent and the furrowing effect 32.

Furthermore, the oxygenated arterial blood in the capillaries beneath the skin furrows 32 allows for, in the subset of patients with chronic venous insufficiency, the "healing of venous stasis dermatitis." Venous stasis dermatitis occurs, in simple terms, because of oxygen starvation that occurs when fat beneath the skin is inundated by deoxygenated venous blood. Garments or dressings 10 created from the fabric 12 according to the present disclosure generate significant tissue pressures. The present disclosure focuses this pressure deep below the skin and delivers pressure that may result in the skin seeing approximately two to three times more tissue oxygen than with known compression devices. Physiologically, the tissue oxygen tension (PaO2) increases from approximately 30 to 38 Torr in venous stasis disease to 80 to 101 Torr when the present disclosure is utilized. The skin inflammation of venous stasis disease is called stasis dermatitis. Increased tissue oxygen pressure heals stasis dermatitis. Increased oxygen beneath the skin furrow 32 leads to cells being able to "repair" themselves. Redness disappears. Hair follicles begin to produce hair in areas under treatment. Skin ulcers heal. This healing of venous stasis ulcers with the present disclosure is dramatic when contrasted with older compression therapy devices. Older compression devices deliver compression to the entire surface of the extremity. Because of this, functional tissue pressure is ineffectively low in older compression devices.

The spaces between the longitudinal wales 14 are beneficial to the patient in at least five ways.

First, the spaces between the longitudinal wales 14 allow for evaporation of perspiration. Older compression garments can became wet with sweat. This trapped moisture can cause skin maceration. Macerated skin greatly increases the risk and potential for skin shear injuries and skin infection with bacteria or fungus.

Second, the spaces between longitudinal wales 14 allow for the radiation of body heat. Garments or dressings 10 produced with the fabric 12 according to the present disclosure remain cool and comfortable to wear in warm environments. Comfort enhances patient compliance. Older compression garments are extremely uncomfortable to wear in hot weather, making patient compliance poor.

Third, the spaces between the longitudinal wales 14 allow for the longitudinal wales 14 to press into the skin creating the previously discussed skin furrows. The skin between the furrows is in a zone of no pressure. In the no pressure zone, the lymphatic and the venous vessels remain open. Lymphatic flow and venous flow can continue uninhibited toward the heart in the no pressure zone. Garments or dressings 10 produced with the fabric 12 according to the present disclosure do not create the tourniquet effect that is common in older compression garments. This tourniquet effect may be the greatest shortcoming of existing compression garments. The circumferential skin constriction of older compression devices blocks lymphatic and venous return to the heart. This tourniquet effect can actually contribute to the pathological condition that the older compression garment was prescribed to treat.

Fourth, the spaces between the longitudinal wales 14 allow for non-compressed skin between the longitudinal wales 14 and skin furrows. This non-compressed skin allows the longitudinal wales 14 to focus a halo of tissue compressive pressure deep into the fat below the skin. The no pressure zone enables the halo of physiologically significant tissue pressure to deeply penetrate the fat beneath the skin. Deep penetration encourages rapid tissue healing and rapid resolution of edema and other treatable conditions.

Fifth, when a garment or dressing 10 produced with the fabric 12 according to the present disclosure is removed for bathing (or other reasons) and replaced, the skin furrows and the non-compressed skin in the no pressure zones are rearranged. This routine change in the location of the skin furrows delivers therapeutic tissue compressive pressure to essentially all of the cells in the extremity roughly about 40% of the time. Thus, all of the cells in the skin and the fat tissue receive the benefit of high tissue pressures delivered in the halos that penetrate deeply beneath the longitudinal wale 14 fibers. In older compression devices, the tissue pressure is constant, but low, to all areas of the skin beneath the compression device.

The secondary or lateral elastomeric threads 16 of the present disclosure have at least five benefits.

First, the lateral threads 16 are (physiologically) not in contact with the skin. In some instances, the plurality of secondary transverse elastomeric threads 16 are formed with an amount of space between at least two of plurality of secondary transverse elastomeric threads 16 adequate to provide evaporation of perspiration and radiation of body heat. Thus, the lateral threads 16 may not prevent evaporation of perspiration, or trap body heat.

Second, the lateral threads 16 are not tightly woven in the fabric 12. There is less lateral wale 16 per unit area than in older compression garments. The lateral elastomeric threads 16 give or stretch easily. This easy stretching makes garments or dressings 10 produced with the fabric 12 of the present disclosure easy to put on and easy to remove. This increases patient compliance. No special jigs are required to put the garment on, such as is often required in older compression garments. Elderly, frail, patients with poor vision can remove and replace the compression garment 10 easily by simply pulling it on and off.

Third, the secondary or lateral elastomeric threads 16 help to prevent the risk of shearing injury to the skin. The fabric 12 of the present disclosure does not cause shearing injury to frail skin during the dangerous periods when compression garments are put on and removed. This is an improvement over older compression garments.

Fourth, the lateral secondary threads 16 are fixed in place between the longitudinal wales 14. The fluffy longitudinal wales 14 stent individual skin cells and the longitudinal wales 14 remain more or less stationary or in place during extremity motion. For instance, the plurality of secondary transverse elastomeric threads 16 disposed between at least two of the plurality of substantially parallel primary wales 14 and substantially equally spaced about a length of the plurality of primary wales 14 may lengthen and shorten during extremity motion of a wearer and generate a dynamic change in tension translatable into a compressive force on the plurality of substantially parallel primary wales 14 suitable for acting as a dynamic pump for at least one of a lymphatic vessel or a vein under a region of skin of a wearer. Extremity motion may transfer energy to the lateral threads 16 as the lateral threads 16 are stretched between the longitudinal wales 14. Extremity motion causes the lateral elastic threads 16 between the stationary longitudinal wales 14 to shorten and lengthen. This shortening and lengthening of the lateral threads 16 generates compressive force on the primary or longitudinal wales 14. This shortening and lengthening of the lateral wales 14 16 generates a dynamic compressive pressure experienced by the skin in furrows beneath the wales 14. This dynamic compressive pressure acts as an engine that translates extremity motion into compressive force and further acts as a dynamic pump for the lymphatic vessels 36 and the small veins under the skin.

With extremity motion, therefore, the present disclosure generates a dynamic change in tissue pressure that results in a pumping action in the veins and the lymphatics in the fat beneath the skin.

Fifth, the lateral elastic threads 16 generate compressive forces that are focused by the longitudinal wales 14. Garments or dressings 10 made from the fabric 12 of the present disclosure have more "give" than traditional compression garments and are therefore more comfortable to wear than known compression garments. The patient does not have a "tight sensation." As garments or dressings 10 made according to the present disclosure are comfortable to wear, patient compliance is high. This "comfort factor" is in marked contrast to older compression garments that have an uncomfortable "tight squeeze" feel.

An externally treatable condition of a patient may be treated using the fabric 12. The method generally comprises the steps of providing a compression garment 10 comprised of the fabric 12 as described above, applying the compression garment 10 to an area of the patient having the externally treatable condition such that the compression garment 10 applies pressure to the area of the patient having the externally treatable condition, and removing the compression garment 10 from the area of the patient having the externally treatable condition after a period of time.

In some instances, the forming of a plurality of substantially parallel primary wales 14 in a substantially longitudinal formation may further include forming the plurality of substantially parallel primary wales 14 from a material capable of raising the temperature of a region of skin in contact with the plurality of substantially parallel primary wales 14. The forming the plurality of substantially parallel primary wales 14 from a material capable of raising the temperature of a region of skin in contact with the plurality of substantially parallel primary wales 14 may further include forming the plurality of substantially parallel primary wales 14 from a material capable of raising the temperature of a region of skin in contact with the plurality of substantially parallel primary wales 14 approximately one to three degrees Fahrenheit.

The forming a plurality of secondary transverse elastomeric threads 16 between at least two of the plurality of substantially parallel primary wales 14 and substantially equally spaced about a length of the plurality of primary wales 14 may further include forming the plurality of secondary transverse elastomeric threads 16 from an elastomeric material.

The forming a plurality of secondary transverse elastomeric threads 16 between at least two of the plurality of substantially parallel primary wales 14 and substantially equally spaced about a length of the plurality of primary wales 14 may further include forming an amount of space between at least two of plurality of secondary transverse elastomeric threads 16 adequate to provide evaporation of perspiration and radiation of body heat. The forming a plurality of secondary transverse elastomeric threads 16 between at least two of the plurality of substantially parallel primary wales 14 and substantially equally spaced about a length of the plurality of primary wales 14 may further include forming the plurality of secondary transverse elastomeric threads 16 in a configuration fixing the plurality of secondary transverse elastomeric threads 16 in place between the plurality of substantially parallel primary wales 14. The forming a plurality of secondary transverse elastomeric threads 16 between at least two of the plurality of substantially parallel primary wales 14 and substantially equally spaced about a length of the plurality of primary wales 14 may further include forming the plurality of secondary transverse elastomeric threads 16 between at least two of the plurality of substantially parallel primary wales 14 and substantially equally spaced about a length of the plurality of primary wales 14 from a material configured to lengthen and shorten during extremity motion of a wearer and generate a dynamic compressive pressure translatable into a compressive force on the plurality of substantially parallel primary wales 14. The forming the plurality of secondary transverse elastomeric threads 16 between at least two of the plurality of substantially parallel primary wales 14 and substantially equally spaced about a length of the plurality of primary wales 14 from a material configured to lengthen and shorten during extremity motion of a wearer and generate a dynamic compressive pressure translatable into a compressive force on the plurality of substantially parallel primary wales 14 may further include forming the plurality of secondary transverse elastomeric threads 16 between at least two of the plurality of substantially parallel primary wales 14 and substantially equally spaced about a length of the plurality of primary wales 14 from a material configured to lengthen and shorten during extremity motion of a wearer and generate a dynamic compressive pressure translatable into a compressive force on the plurality of substantially parallel primary wales 14 suitable for acting as a dynamic pump for at least one of a lymphatic vessel or a vein under a region of skin of a wearer.

The forming a plurality of secondary transverse elastomeric threads 16 between at least two of the plurality of substantially parallel primary wales 14 and substantially equally spaced about a length of the plurality of primary wales 14 may further include forming an amount of space between at least two of the plurality of substantially parallel primary wales 14 adequate to provide a pressure differential between a region of skin in contact with at least one of the plurality of substantially parallel primary wales 14 and a region of skin covered by the plurality of secondary transverse elastomeric threads 16. The forming an amount of space between at least two of the plurality of substantially parallel primary wales 14 configured to provide a pressure differential between a region of skin in contact with at least one of the plurality of substantially parallel primary wales 14 and a region of skin covered by the plurality of secondary transverse elastomeric threads 16 may further include forming an amount of space between at least two of the plurality of substantially parallel primary wales 14 applying a nontherapeutic amount of pressure to a region of a wearer covered the plurality of secondary transverse elastomeric threads 16. The forming an amount of space between at least two of the plurality of substantially parallel primary wales 14 adequate to provide a pressure differential between a region of skin in contact with at least one of the plurality of substantially parallel primary wales 14 and a region of skin covered by the plurality of secondary transverse elastomeric threads 16 may further include forming an amount of space between at least two of the plurality of substantially parallel primary wales 14 adequate to create an amount of tension causing the plurality of substantially parallel primary wales 14 to apply a substantially continuous amount of pressure to a region of a wearer covered by the plurality of substantially parallel primary wales 14.

The forming an amount of space between at least two of the plurality of substantially parallel primary wales 14 adequate to provide an amount of compression causing the plurality of substantially parallel primary wales 14 to apply a substantially continuous amount of pressure to a region of a wearer covered by the plurality of substantially parallel primary wales 14 may further include forming an amount of space between at least two of the plurality of substantially parallel primary wales 14 adequate to provide an amount of tension causing the plurality of substantially parallel primary wales 14 to apply an amount of pressure sufficient to create a skin furrow within a region of a wearer covered by the plurality of substantially parallel primary wales 14.

Figure 4:
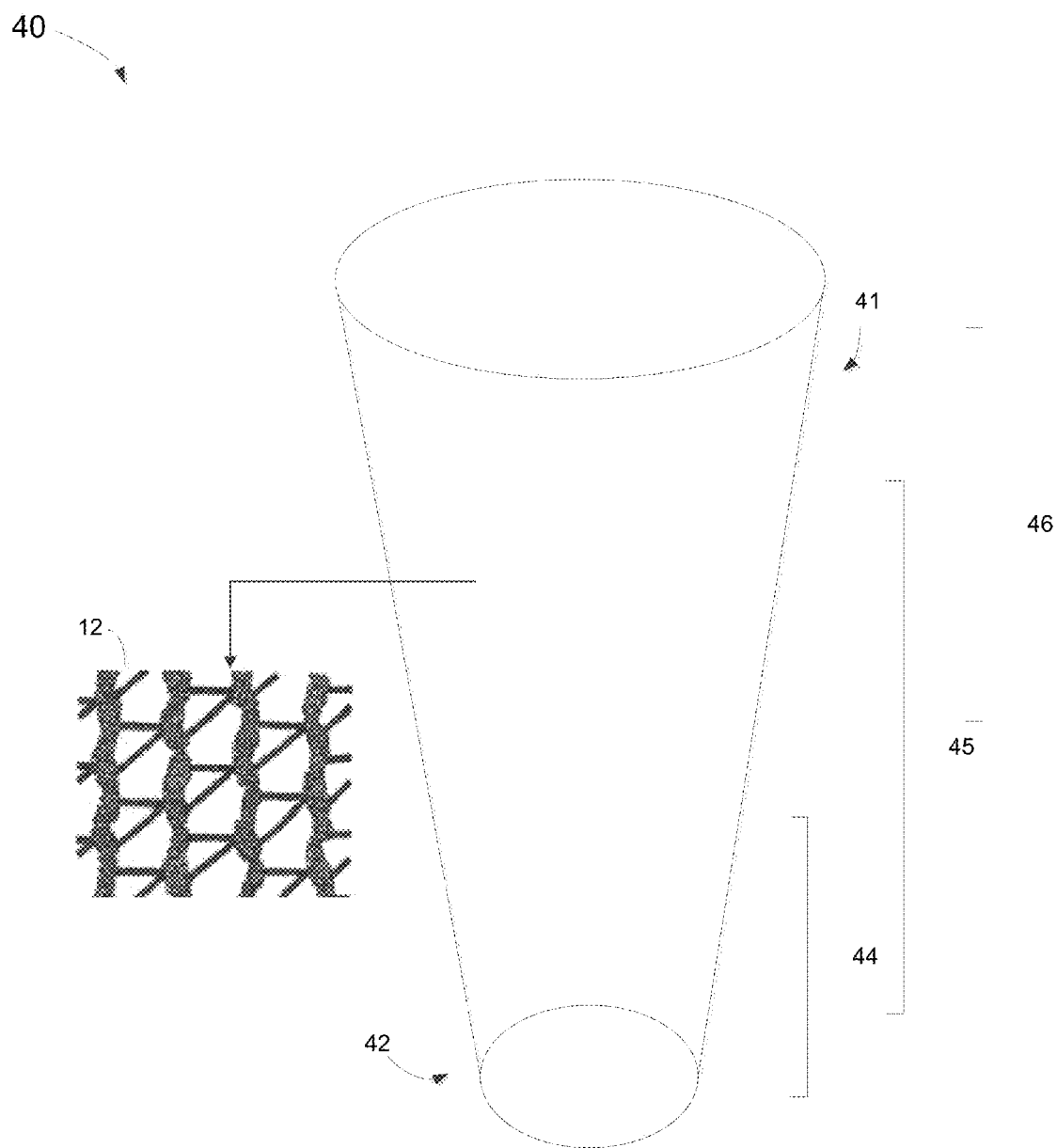
FIG. 4 is an embodiment of a graduated compression garment according to the present disclosure having a generally conical form.
Figure 8:
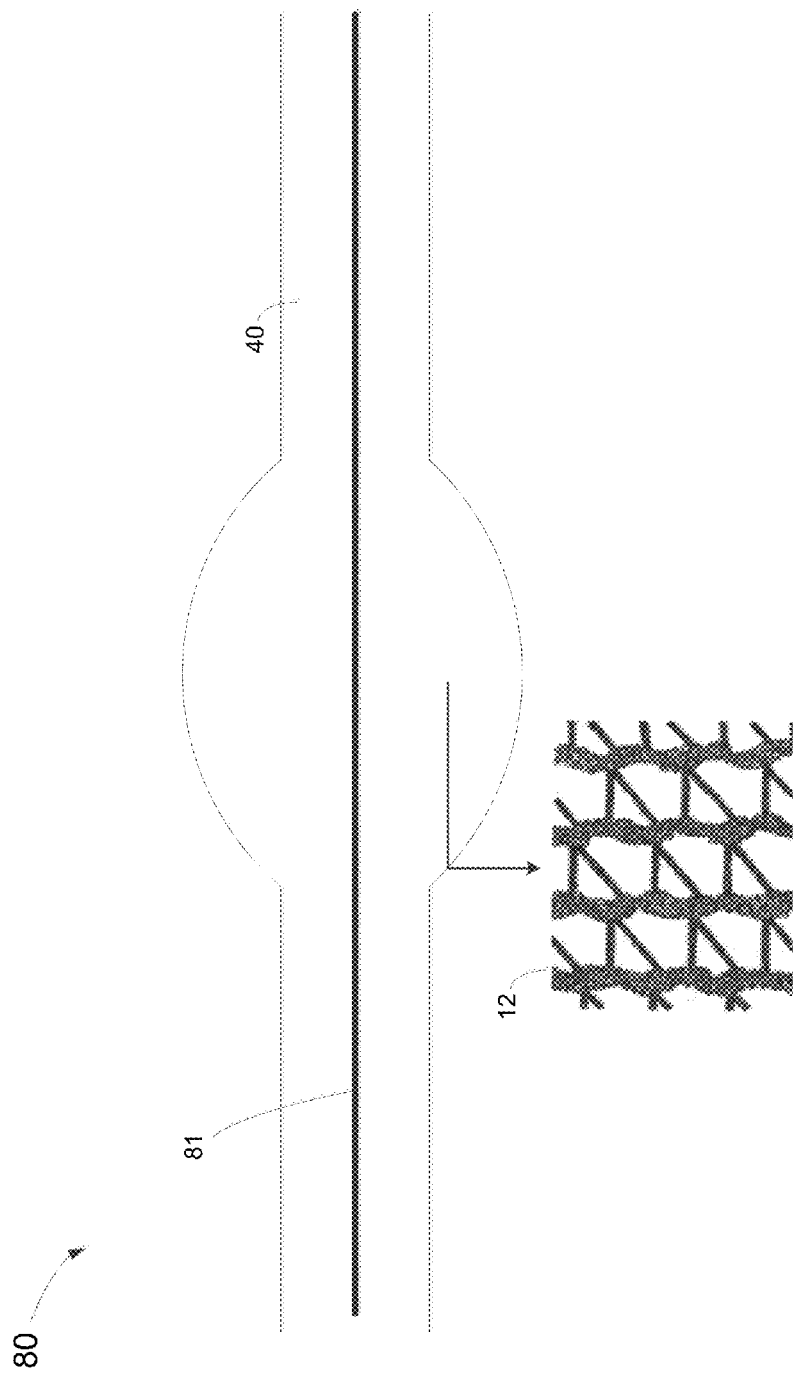
FIG. 8 is a side view of an embodiment of a length graduated compression garment according to the present disclosure suitable for trimming.

Further embodiments of the present disclosure may to provide a substantially tubular graduated compression garment 40. FIG. 4 illustrates an embodiment of a graduated compression garment 40 according to the present disclosure having a generally conical form. FIG. 8 is a side view 80 of an embodiment of a length graduated compression garment according to the present disclosure suitable for trimming. A graduated compression garment 40 refers to a compression garment as described above having elastic tension that delivers compression which gradually decreases from distal to proximal. For instance, the compression garment may deliver higher compression levels at the ankle, when limb is a leg, and may gradually decrease pressure moving proximally toward the groin. Higher compression at the ankle may drive water up the limb proximally toward the heart. Specifically, graduated compression, with physician prescribed compression levels, as measured in millimeters of mercury, may provide increased compressive elastic force at a first (smaller) limb end (an ankle, when the limb is a leg) and gradually decreasing levels of compressive force moving proximally toward the a second (larger) limb end (e.g., the groin). For example, the tubular graduated compression garment 40 may deliver a known level of compression, (e.g., about 25 millimeters of mercury), measured with a blood pressure cuff, at the ankle to encourage the return of venous blood and lymphatic fluid in the subcutaneous fat, toward the heart. A single pigmented fiber 81 may be employed within the graduated compression garment 40 to allow for easy orientation of parallel longitudinal fuzzy wales 14 on the long axis of the limb. Additional embodiments are contemplated suitable for other body parts. For instance, a sock-type graduated compression garment may be formed having at least a portion of the sock formed using graduated compression techniques discussed herein. In some embodiments, the primary (fuzzy) wales 14 are approximately 150% thicker than those described above. In further additional embodiments, the primary wales 14 have a diameter ranging from about 1.2 to about 1.7 mm, or from about 2.2 to about 2.5 mm. Larger diameters (e.g., 2.6 mm and above) are also contemplated.

As discussed herein, the graduated compression garment 40 is configured to apply compression on about one fifth of a covered skin surface. The graduated tubular compression garment may thus be highly effective to move water out of the subcutaneous fat. Accordingly, the graduated tubular compression garment may assist with the prevention and treatment of edema and other conditions that cause swelling.

The graduated tubular compression garment disclosed herein includes a plurality of longitudinal fuzzy wales 14 arranged to form a fabric 12 with a plurality of transverse elastomeric spandex threads 16 under variable tension connecting the adjacent fuzzy longitudinal wales 14. The fabric 12 may be as described in FIG. 1. The graduated tubular compression garment may be formed in such way as to deliver high levels of elastic compression distally on the limb gradually decreasing in elastomeric tension and elastic compression pressure as the limb increases in diameter proximally. To this end, graduated tubular compression garment may include a first end 41 and a second end 42. The fuzzy longitudinal wales 14 may be under decreasing tension from small diameter to large diameter, to deliver, when on an extremity such as the lower limb, decreasing compression of the subcutaneous fat, distal to proximal.

To deliver high compression distally where the tubular compression garment has a small diameter and low elastic tension proximally where the tubular compression garment has a larger diameter the tension on the elastomeric yarns is "graduated" in a manner that delivers graduated elastic tension, distal to proximal, that generates graduated compression of the skin and underlying subcutaneous fat. Thus, the graduated tubular compression garment may be formed substantially as a cylindrical or tubular shaped garment and may further include a plurality of substantially parallel longitudinal fuzzy wales 14, that maintain uniform fuzzy warp knitted wale diameters under decreasing, graduated elastic tension, distal to proximal, delivered by a plurality of secondary elastic-type (e.g., spandex) elastomeric threads 16 with gradually decreasing tension while at rest, (not deployed on an extremity), under no distention, in the graduated compression garment 40 or deployed as a graduated compression garment 40 on an extremity. When the graduated tubular compression garment is deployed on a limb, the distance between parallel wales 14 increases slightly as limb diameter increases without deforming the diameter or surface architecture of the fuzzy wales 14 in contact with the skin and underlying subcutaneous fat. The plurality of substantially primary wales 14 and the plurality of secondary elastomeric threads 16, knitted on a warp knitting machine, form the plurality of substantially parallel primary wales 14 that are under continuously decreasing elastic tension, distal to proximal, in a manner to form a garment that has a small distal diameter when employed on a limb distally that gradually enlarges to a larger diameter on the proximal limb. The diameter of the fuzzy wale remains uniform in spite of differing elastomeric fiber tension. Each of the plurality of substantially parallel primary wales 14 is formed from a material having a fuzzy outer surface that is of uniform diameter while delivering graduated elastic tension.

Figure 5:
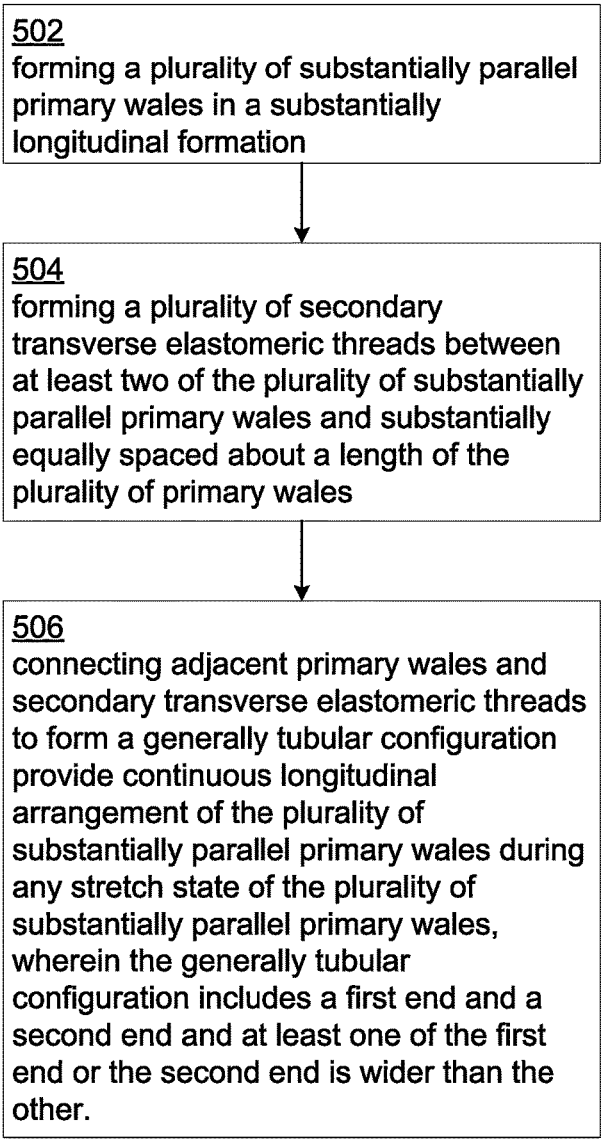
FIG. 5 is a flow diagram illustrating a method for forming a graduated compression garment according to an embodiment of the disclosure.

Referring to FIG. 5, a flow diagram illustrating a method 500 for forming a graduated compression garment 40 according to an embodiment of the disclosure is shown. Method 500 may be utilized to form embodiments of the compression garment as described above. In a preferred embodiment, the method 500 for forming a fabric includes, but is not limited to forming 502 a plurality of substantially parallel primary wales 14 in a substantially longitudinal formation. The plurality of substantially parallel primary wales 14 may be generally formed as described above. The method 500 may also include forming 504 a plurality of secondary transverse elastomeric threads 16 between at least two of the plurality of substantially parallel primary wales 14 and substantially equally spaced about a length of the plurality of primary wales 14. Such forming may also be performed as generally described above. The method 500 may also include connecting 506 adjacent primary wales 14 and secondary transverse elastomeric threads 16 to form a generally tubular configuration provide continuous longitudinal arrangement of the plurality of substantially parallel primary wales 14 during any stretch state of the plurality of substantially parallel primary wales 14. According to this embodiment, the generally tubular compression garment may be formed with a first end 41 and a second end 42, and at least one of the first end 41 or the second end 42 is wider than the other.

The forming of the plurality of secondary transverse elastomeric threads 16 between at least two of the plurality of substantially parallel primary wales 14 and substantially equally spaced about a length of the plurality of primary wales 14 further includes arranging the plurality of secondary transverse elastomeric threads 16 to connect to adjacent primary wales 14 at an angle greater to or less than 90 degrees with respect to the plurality of substantially parallel primary wales 14. The method may further include utilizing a crisscrossing lateral elastomeric stitch on a warp knitting machine to form the plurality of substantially parallel primary wales 14 and the plurality of secondary transverse elastomeric threads 16. The forming a plurality of substantially parallel primary wales 14 in a substantially longitudinal formation may further include forming the plurality of substantially parallel primary wales 14 from a material having a diameter approximately 11 times larger than a diameter of a material utilized for forming the plurality of secondary elastomeric threads 16. The forming of a plurality of substantially parallel primary wales 14 in a substantially longitudinal formation may further include forming the plurality of substantially parallel primary wales 14 from a material having a fuzzy outer surface.

The graduated compression garment 40 of the present disclosure may prove salutatory for the reversing the pathophysiology and therapeutic for stasis dermatitis in at least the following ways:
1. Decreasing venous hypertension by focusing compression on just 25% of the surface of the skin and subcutaneous fat, leaving open veins for efficient runoff of venous blood and a subsequent decrease in venous hypertension.
2. Decreasing edema fluid in the fat beneath that skin inflamed and swollen due to stasis dermatitis.
3. Removing subcutaneous fat water significantly improves the diffusion of oxygen to skin cells.
Increased levels of oxygen increase the effectiveness of white blood cells to control infection, and increase local healing.
4. Improved lymphatic function resulting from use of the graduated compression garment 40 may dramatically decrease inflammatory mediators (e.g., necrotic fat, enzyme contents of spent white blood cells, matrix metalloproteases, endotoxins and exotoxins from bacteria).

The presently disclosed graduated compression garment 40 may be specifically formed to focus tension between transverse elastomeric fibers that limits compression of the subcutaneous fat in skin at risk due to venous hypertension and stasis dermatitis to about 20 to 30% of the skin surface. This ratio of compressed subcutaneous fat, under the furrows that form beneath the longitudinal fuzzy wales 14, to non-compressed subcutaneous fat between wales 14, is on a continuum of ratios, 1:5, 1:4 or 1:3, depending on the diameter of the limb and the diameter of the tubular graduated compression garment 40. As water is compressed from the subcutaneous fat, furrows (or "corn rows") in the subcutaneous fat may result. In furrows in fat under the wales 14, one or more physiological modifications may occur. For instance, excess water (edema fluid) may drain away from the compressed fat via open lymphatic vessels between the furrows escaping into the lymphatic vessels of the leg muscles beneath the superficial subcutaneous fat. Also, as furrows form beneath wales 14, the fat directly below the fuzzy wale/skin nexus at the furrow's edge may experience relatively high levels of compression. For instance, one millimeter (mm) away from the fuzzy wale skin nexus at the furrows edge, the pressure decreases. Two mm away, the pressure continues to dissipate in the waterlogged fat stewing in deoxygenated venous blood spike with metabolic toxins. Beneath the furrow the elastic compression distributes out into the waterlogged fat in a halo of decreasing pressure, said another way, a pressure gradient radiates out from the fuzzy wales 14 into the subcutaneous fat. Fluid moves from high pressure to low pressure in various via mass movement: diffusion of water in the interstitial fat; via lymphatic vessel outflow; and via venules and veins draining from high pressure to low. In this halo of compressed tissue beneath the fuzzy wales 14, fresh arterial capillary blood circulates easily. Blood rich with nutrients and oxygen resuscitates skin cells harmed by the venous hypertension leading to clearing of stasis dermatitis and healing of venous leg ulcers. Further still, stale deoxygenated venous blood with high levels of lactate and other metabolic waste drain away from the compressed fat in small venules and veins, following the pressure gradient generated by fuzzy wales 14 and compression from elastomeric fiber under tension.

The graduated compression garment 40 or textile of the current disclosure has an elastomeric textile component and a fuzzy textile wale component composed of fine polymer fibers that are knitted. The transverse elastomeric fibers effectively do not touch the skin surface in that they are suspended between the much thicker longitudinal fuzzy wales 14 which are indeed in contact with the skin surface. The elastomeric yarns are under constant tension. The fuzzy longitudinal wales 14 are suspended between the "on tension" elastomeric transverse yarns. When the fuzzy wales 14 rest on skin, the wales 14 may translate the tension from elastomeric components on stretch into compression of the skin.

The present disclosure forms a floating compression tensegrity structure when deployed on the skin. Unique to the present disclosure is a garment that, when deployed (worn) on an extremity, forms a tensegrity structure with the skin. With this tensegrity structure, the graduated compression garment 40 of the present disclosure is designed to move water out of the subcutaneous fat while preserving capillary perfusion of the skin. The graduated compression garment 40 of the present disclosure delivers elastic compression to approximately 20% of the skin surface. Limiting compression to approximately 20% of the skin surface with fuzzy wales 14 under elastic tension, allows for the effective diffusion of oxygen from red blood cells circulating freely in nearby non compressed subcutaneous fat. The fuzzy wale technology of the present disclosure ensures that four fifths of the skin remains highly perfused. Oxygen from well perfused fat easily diffuses into the fraction of skin under compression beneath fuzzy wales 14.

Red blood cells traveling though capillaries in the non-compressed skin adjacent to the compressed skin beneath the fuzzy wales 14 deliver oxygen that diffuses to the compressed skin and subcutaneous fat. Skin beneath fuzzy wales 14 is under elastic compression which creates furrows in the subcutaneous fat. Capillary perfusion of tissue in the furrow under the fuzzy elastic compression wale is decreased. A halo of increased tissue pressure spreads into subcutaneous fat not directly beneath the fuzzy wale. This halo of elastic compression in the subcutaneous fat decreases as the distance from the fuzzy wale increases. The halo of compressed fat creates a pressure gradient in the tissue which improves return of water to the post capillary venules. Having a "low pressure sink" adjacent to tissue compressed by fuzzy wales 14 enhances movement excess water out of the fat. The halo of tissue compression radiates into the adjacent 80% of the skin surface that is not compressed. Non-compressed subcutaneous fat has the advantage of high capillary blood flow to deliver oxygen to the skin. Said another way, fuzzy wale elastic compression limits compression to approximately one fifth of the skin surface. The graduated fuzzy wale compression garment may maintain capillary perfusion in approximately $\frac{4}{5}^{th}$ of the skin. Oxygen delivered to the skin cells in the non-compressed areas diffuses short distances into the compressed tissue. Thus, fuzzy wale graduated compression garment 40 textile functionally does not act as a tourniquet for capillaries under the skin.

In some embodiments, the graduated compression garment 40 of the present disclosure may be engineered specifically to treat painful, inflamed or ischemic skin, or venous insufficiency. Venous insufficiency results when leg vein valves that are scarred open and nonfunctional. Nonfunctional one way tissue valves are unable to harness muscle contraction in the leg, the "muscle pump," to lift blood from the foot back to the heart against gravity. Nonfunctioning valves in the veins of the lower extremity may give rise a number of physiological problems and pathological conditions. Such conditions may include varicose veins (veins that have dilated in response to venous hypertension), venous dermatitis, venous insufficiency dermatitis and venous stasis dermatitis, each of which may defined by painful inflammation of the skin and subcutaneous fat near the skin that occurs with venous hypertension. Venous insufficiency dermatitis appears as swollen bright red painful skin that mimics, for example, a serious soft tissue Streptococcal or Staphylococcal infection. Additional conditions may include venous leg ulcers (VLUs) that may result from neglected untreated venous stasis dermatitis. The compression garment as described above may also substantially reduce or eliminate dyshidrosis, skin maceration, bacterial overgrowth and/or the formation of ulcers in at risk wearers. A lighter graduated compression garment may be provided that delivers low compression via large diameter wales under a pressure of about 5 to 10 mm of mercury (versus 20 to 30 mm). Such embodiments may utilize the previously discussed primary wales 14 have a diameter ranging from about 2.2 to about 2.5 mm.

Figure 9:
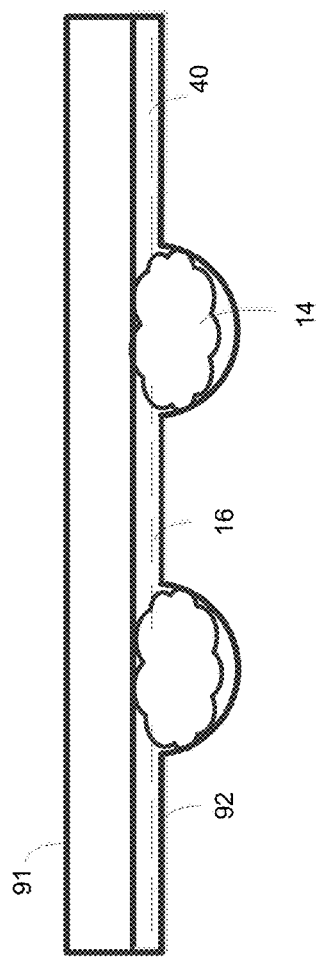
FIG. 9 is a side view of an embodiment of a graduated compression garment according to the present disclosure incorporated with a brace.

The garment may be comfortable to wear and may be effective in decreasing skin shear injury when worn under skin appliances such as articulated knee braces or military ceramic body armor. FIG. 9 is a side view of an embodiment of a graduated compression garment according to the present disclosure incorporated with a brace. Accordingly, embodiments of the present disclosure may also be used to provide skin appliance protection (e.g., the protection of the skin under external appliances) and to improve the effectiveness of the fuzzy wale graduated compression garment 40 to decrease inflammation and disperse water away from the skin under external appliances. As seen in FIG. 9, an appliance 91 may be in contact with a compression garment (e.g., graduated compression garment 40). The skin 92 is also in contact with the compression garment. A fuzzy wale 93 may be impressed into the skin 92 and may create a furrow in the skin 92 as a result of compression delivered by the transverse spandex elastic yarns 94. The fiber loops of the fuzzy wale may 93 may extend over the edges of the furrow creating a slippery interface between the skin 92 and the appliance 91.

The compression garment may be integrated with one or more appliances (e.g., braces, casts, armor, etc.) to provide skin protection. The graduated compression garment 40 may be worn as a first layer under removable orthopedic devices such (e.g., removable cam walkers) to immobilize sprained/fractured ankles, metal hinged knee braces for chronic knee internal derangements, and Kevlar and ceramic military body armor, may prevent damage to the skin. Specifically, embodiments of the present disclosure may also provide an stretchable compression garment with fuzzy wale fibers modified to: protect the skin from chaffing (skin shear injury) when worn under, for example articulated metal orthopedic braces where skin shear commonly breaks down skin; protect the skin from moisture damage when external appliances are worn in hot environments such as military ceramic and polymer body armor; protect macerated skin under orthopedic appliances and body armor from bacterial overgrowth; and prevent ulcers and painful wound forming in macerated skin under the appliance.

According to further embodiments, the graduated compression garment 40 may provide decreased bacterial over growth on the skin. In one embodiment, the graduated compression garment 40 may be impregnated with fibers of one or more Group 11 periodic table transition metals. Such a graduated compression garment 40 having embedded Group 11 periodic table transition metal fibers may also decrease odor when worn. In some instances, the graduated compression garment 40 includes any antimicrobial metal providing a germ and microbial free environment within the garment and treated areas. For instance, the graduated compression garment 40 may be loaded with at least one metallic antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures or combinations thereof. Any known methods may be used to impart durable antimicrobial activity to the graduated compression garment 40 provides effective, durable, and long-lasting antimicrobial characteristics for the garment surfaces.

Although the above descriptions and figures focus primarily on treating the extremities, wounds, swelling or any other condition described above that may be located on the torso, head or other area of the body may also be treated using the graduated compression garment 40 according to the present disclosure.

Figure 6A:
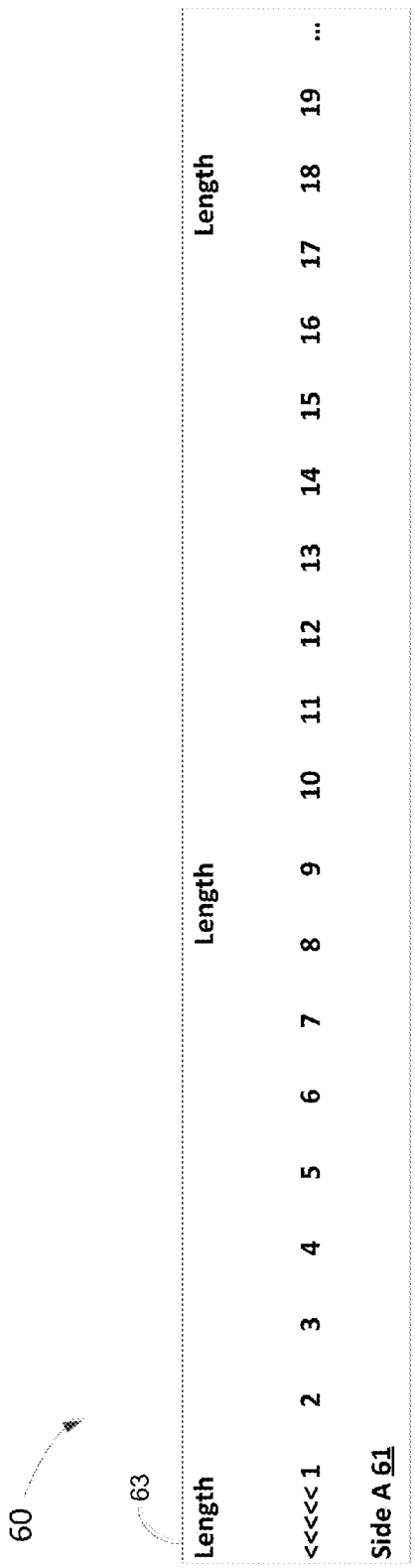
FIGS. 6A and 6B are diagrams illustrating an apparatus for forming a compression garment according to an embodiment of the disclosure.
Figure 6B:
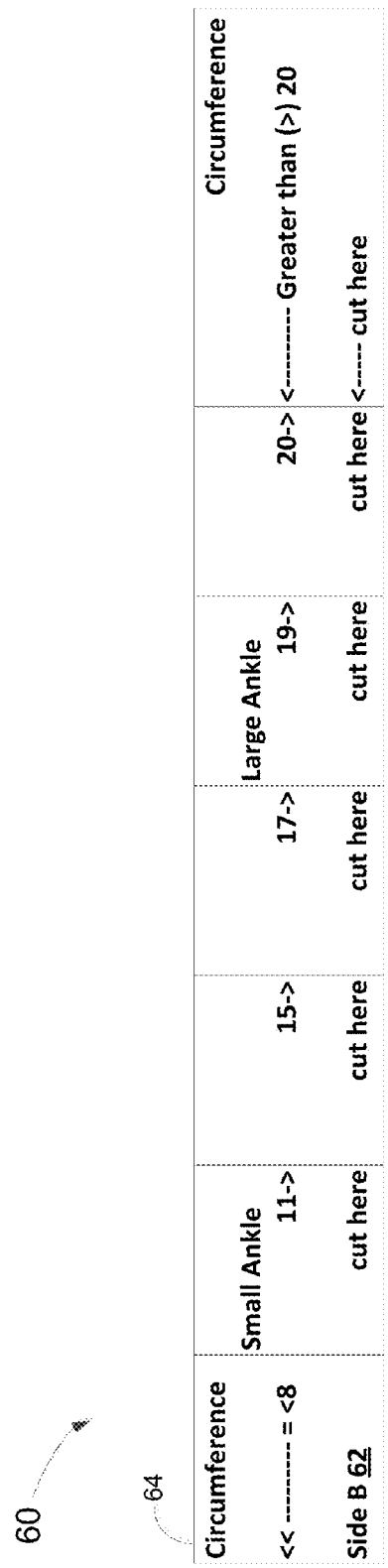

According to further embodiments of the present disclosure, a measuring device for measuring and preparing a graduated length compression garment as described above is disclosed. FIGS. 6A and 6B illustrate a measuring device 60 according to embodiments of the present disclosure. FIG. 6A illustrates a first side of the measuring device 60 that may be used to measure limb diameter at it largest. FIG. 6B illustrates a second side of the measuring device 60, that may be used to measure limb circumference (e.g., calf, thigh, or forearm circumference). In preferred embodiments, the measuring device 60 may provide a custom fitting compression garment that delivers a prescribed level of graduated elastic compression (e.g., say 25 millimeters of mercury at the ankle) cut from a long segment of tubular graduated compression garment 40 fabric. The measuring device 60 may enable the graduated compression garment 40 to be precisely fitted on an extremity, trimmed as necessary from a longer cone shaped graduated compression garment 40, to provide a known amount, a "prescribed" amount of elastic compression to the skin and underlying fat. For instance, as shown in FIG. 4, a first segment 44 may be cut for a smaller patient, a second segment 45 may be cut for an average sized patient, and a third segment 46 may be cut for a larger patient.

The device 60 may be formed as a strip (e.g., tape) and may a first side (Side A) 61 and a second side (Side B) 62, each including substantially equally spaced increments, measured in inches or centimeters. In some instances, first side 61 and second side 62 are opposite sides of a strip or tape (e.g., a front and back of the strip). The measuring device 60 provides a mechanism for custom fitting a length of tubular graduated compression garment 40 such that a shorter segment is provided based on a wearer's needs or desired. For instance, a patient with thin ankle and calf may benefit from a segment of product selected from the lower/thinner segment of the graduated compression garment length. A patient with a thicker ankle may find the above segment too tight and thus may benefit from a segment cut further up the tube where the circumference is larger. The compression garment measuring device 60 may translate measurements of limb circumference and limb length to a visual indication of where to trim a larger portion of tubular graduated compression garment 40 to provide accurate and/or desired first and second end circumference and length. The measuring device 60 may also be portable and/or disposable.

The measuring device 40 provides for custom fitting a garment to deliver, at varying portions of a limb, known amounts of elastic compression. In some instances, the known amounts of elastic compression may range between about 20-30 millimeters of mercury. The custom fitted gradated compression garment may be provided by trimming a specific length from a longer graduated compression garment 40. The measuring device 60 further provides selection a specific length of a 36 inch long shaped graduated fuzzy wale focused elastic compression tubular compression garment textile, to be positioned precisely on the leg using a specific anatomic land mark for example, the patella, the widest part of the calf, or the ankle malleoli bony protuberances. The measuring device 60 also provides placement the shaped fuzzy graduated elastic compression tubular compression garment to deliver and known level of graduated therapeutic fuzzy wale focused compression, at a given anatomic site, say the widest part of the calf, in a manner that enhances the function of the sub cutaneous lymphatic system to remove water from the subcutaneous fat and return it to the vascular system by lymphatic vessels.

Using the second side 62, a circumference measurement may be used to determine how much of the distal, small diameter portion of the compression garment length to trim. The large diameter end of the graduated compression garment may be trimmed after a wearer dons the compression garment. For instance, a garment worn on a leg may be trimmed depending on how far above the knee cap the wearer or care giver desires the compression garment to span. For example, in the instance of a smaller graduated compression garment 40, a first end 64 may be lined up with the distal end of the compression garment. If, for example, a wearer's calf is 17 inches in diameter, the second side of the measuring device 60 may mark the length of the compression garment from a first point to a second point.

The measuring device 60 enables precise placement the shaped fuzzy, graduated elastic compression tubular compression garment to deliver and known level of graduated therapeutic fuzzy wale focused compression, at a given anatomic site, (e.g., the widest part of the calf), in a manner that enhances the function of the sub cutaneous lymphatic system to remove water from the subcutaneous fat and return it to the vascular system by lymphatic vessels. For instance, with respect to measuring a length of graduated compression garment 40 for a leg, the device may enable a practitioner or patient to select a specific length of a 36 inch long shaped graduated fuzzy wale focused elastic compression tubular compression garment textile, to be positioned precisely on the leg using a specific anatomic land mark for example, the patella, the widest part of the calf, or the ankle malleoli bony protuberances.

Figure 7:
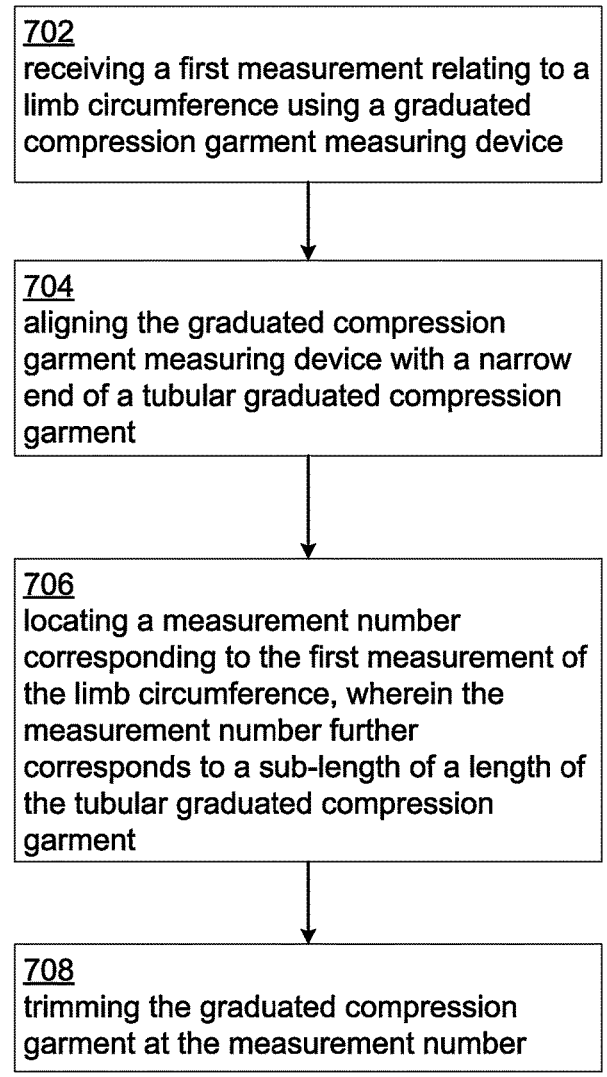
FIG. 7 is a flow diagram illustrating a method for forming a compression garment according to an embodiment of the disclosure.

Referring to FIG. 7, a flow diagram illustrating a method 70 for forming a graduated compression garment according to an embodiment of the disclosure is shown. A method for providing a custom length of tubular graduated compression garment may include receiving 702 a first measurement relating to a limb circumference. For example, a wearer or caregiver may measure the circumference of a limb with, for instance, the first side of the measuring device 60. Using the leg as a specific example, a first measurement may be a circumference of an ankle using the second side 61 of the measuring device 60. The measuring device 60 may then be aligned 704 (e.g., positioning the arrow end 63 of the first side down) with the narrow end of the tubular graduated compression garment 40. Using the first side 61, measurement number corresponding to the ankle circumference may be located 706. The measurement number further corresponds to a sub-length of a length of the tubular graduated compression garment. The method 70 may further include initiating 708 the trimming of the graduated compression garment measuring at a location on the graduated compression garment measuring device corresponding with the measurement number. Alternatively, the method 70 may include receiving instructions to initiate the trimming of the graduated compression garment. The tubular graduated compression garment 40 may be trimmed at, for instance, level 17. A desired length may also be measured using the measuring device 60. For example, a distance from a first limb portion (e.g., an ankle) to a second limb portion (e.g., an upper knee) may be measured using the first side 61 of the measurement device. The measuring device 60 may then be aligned with the narrowest portion of the tubular graduated compression garment 40. A measurement number corresponding to length may be located on the first side 61 of the measuring device 60. The tubular graduated compression garment 40 may then be trimmed at this location. In some instances, method 70 may be implemented by computer readable storage media (e.g., a storage device, tangible storage media, etc.), and may be implemented within a system (e.g., computer) including a memory and a processor.

While the specific embodiments have been illustrated and described, numerous modifications come to mind without significantly departing from the spirit of the disclosure, and the scope of protection is only limited by the scope of the accompanying claims.

What is claimed:

1. A graduated compression garment comprising: a plurality of longitudinal fuzzy wales arranged to form a fabric with a plurality of transverse elastomeric threads under variable tension connecting the adjacent longitudinal fuzzy wales to deliver a first level of elastic compression distally on a limb and a gradually decreasing level of elastic compression as the limb increases in diameter proximally, the plurality of longitudinally fuzzy wales formed from a material having a diameter approximately 11 times larger than a diameter of a material utilized for forming the plurality of transverse elastomeric threads, wherein a continuous longitudinal arrangement of the plurality of longitudinal fuzzy wales is maintained during any stretch state of the plurality of longitudinal fuzzy wales.

2. The compression garment of claim 1, wherein the longitudinal fuzzy wales are under decreasing tension from small diameter to large diameter, to deliver, when on an extremity, decreasing compression of the subcutaneous fat, distal to proximal.

3. The compression garment of claim 1, wherein the each of plurality of longitudinal fuzzy wales is substantially parallel to one another and maintain a uniform diameter while delivering decreasing, graduated elastic tension, distal to proximal via the plurality of transverse elastomeric threads.

4. The compression garment of claim 3, wherein each of the plurality of substantially parallel longitudinal fuzzy wales and the plurality of transverse elastomeric threads is knitted on a warp knitting machine and the plurality of substantially parallel longitudinal fuzzy wales are under substantially continuously decreasing elastic tension, distal to proximal.

5. The compression garment of claim 3, wherein each of the plurality of substantially parallel longitudinal fuzzy wales is formed from a material having a fuzzy outer surface that is of uniform diameter while delivering graduated elastic tension.

6. The compression garment of claim 1, wherein, when deployed on a limb, the distance between each of the plurality of longitudinal fuzzy wales, increases slightly as limb diameter increases without deforming the diameter or surface architecture of the fuzzy wales in contact with the skin and underlying subcutaneous fat.

7. The compression garment of claim 1, wherein the plurality longitudinal fuzzy wales are arranged to deliver low levels of elastic compression pressure to painful inflamed skin at risk from venous stasis dermatitis, cellulitis, ischemic dermatitis and lymphedema.

8. The compression garment of claim 1, further including fibers of one or more Group 11 periodic table transition metals impregnated within the plurality of longitudinal fuzzy wales.

9. The compression garment of claim 1, wherein the plurality of transverse elastomeric threads are connected to adjacent fuzzy wales at an angle greater to or less than about 90 degrees with respect to the plurality of longitudinal fuzzy wales, wherein the plurality of transverse elastomeric threads are formed to provide an amount of space between at least two of the plurality of longitudinal fuzzy wales adequate to provide a pressure differential between a region of skin in contact with at least one of the plurality of longitudinal fuzzy wales and a region of skin covered by the plurality of transverse elastomeric threads.

10. The compression garment of claim 9, wherein the fabric provides a compression comprising at least twenty-five millimeters of mercury distally on the limb.

* * * * *